United States Patent
Corley

(10) Patent No.: US 9,256,804 B2
(45) Date of Patent: Feb. 9, 2016

(54) LIGHT SOURCE COMPARATOR AND CALIBRATION APPARATUS

(71) Applicant: Ferrand D. E. Corley, Mississauga (CA)

(72) Inventor: Ferrand D. E. Corley, Mississauga (CA)

( * ) Notice: Subject to any disclaimer, the term of this patent is extended or adjusted under 35 U.S.C. 154(b) by 153 days.

(21) Appl. No.: 13/986,205

(22) Filed: Apr. 12, 2013

(65) Prior Publication Data

US 2013/0272603 A1 Oct. 17, 2013

Related U.S. Application Data

(60) Provisional application No. 61/686,847, filed on Apr. 13, 2012.

(51) Int. Cl.
| | |
|---|---|
| *G01J 3/52* | (2006.01) |
| *G06K 9/62* | (2006.01) |
| *G01J 3/46* | (2006.01) |
| *G01N 21/29* | (2006.01) |
| *H04N 1/40* | (2006.01) |

(52) U.S. Cl.
CPC ............... *G06K 9/6202* (2013.01); *G01J 3/463* (2013.01); *G01J 3/52* (2013.01); *G01J 3/522* (2013.01); *G01N 21/293* (2013.01); *H04N 1/40056* (2013.01)

(58) Field of Classification Search
CPC ............. G01J 3/52; G01J 3/522; G01J 3/463; G01N 21/293
See application file for complete search history.

(56) References Cited

U.S. PATENT DOCUMENTS

| | | | | |
|---|---|---|---|---|
| 1,566,046 | A * | 12/1925 | Sleight | 356/422 |
| 1,597,830 | A * | 8/1926 | Rueger | 356/422 |
| 2,124,229 | A * | 7/1938 | Ferree et al. | 351/239 |
| 2,240,053 | A * | 4/1941 | Richardson | 356/423 |
| 4,112,594 | A * | 9/1978 | Impastato | 434/104 |
| 4,657,399 | A * | 4/1987 | Hall | 356/421 |
| 4,779,136 | A * | 10/1988 | Corley | 348/188 |
| 6,112,665 | A * | 9/2000 | Teter et al. | 101/483 |
| 6,139,325 | A * | 10/2000 | Tracy et al. | 434/104 |
| 2003/0156194 | A1 * | 8/2003 | Sugiura et al. | 348/187 |
| 2007/0002143 | A1 * | 1/2007 | Elberbaum | H04N 17/002 348/188 |
| 2009/0097028 | A1 * | 4/2009 | Vogh, Jr. | G01J 3/46 356/407 |
| 2010/0253946 | A1 * | 10/2010 | Corley | 356/421 |

* cited by examiner

*Primary Examiner* — Michael A Lyons

(57) ABSTRACT

An apparatus for identifying differences in the visual and recorded appearance of colors and gray tones illuminated by light sources having different spectral distribution and having: a first image with illumination, with separate and different color elements and with gray scale elements, apertures in the first image adjacent to the elements, a second image with illumination having a plurality of separate elements of color and gray scale, corresponding to the elements of the first image so that the elements on the second image are viewable through the apertures in the first image, with corresponding color and gray scale elements adjacent to one another in the first and second images, and a method of comparing light quality using such apparatus.

7 Claims, 5 Drawing Sheets

Figure 1:
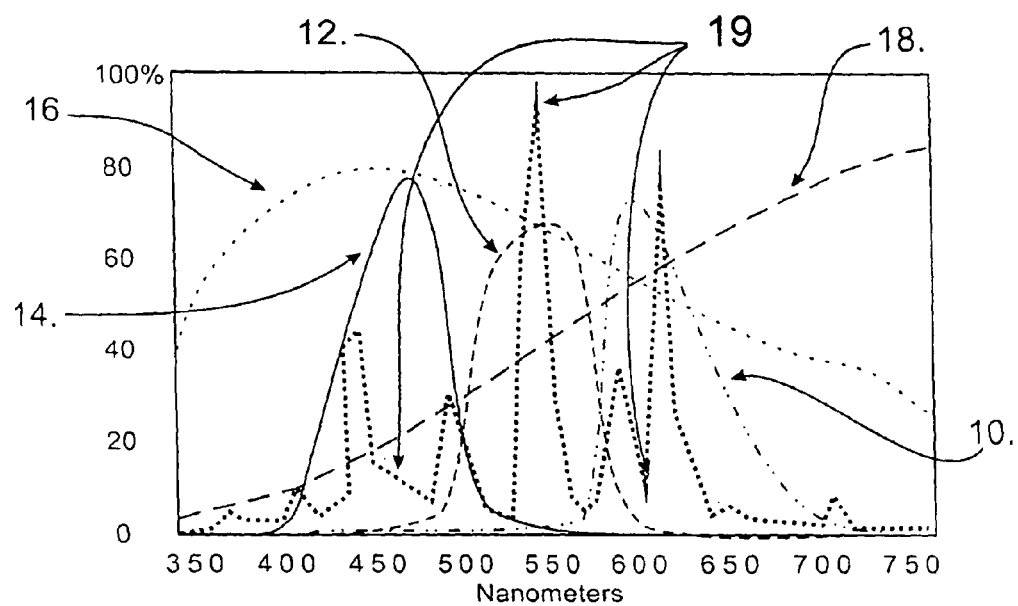

LIGHT SOURCE COMPARATOR AND CALIBRATION APPARATUS

This invention is based on U.S. Provisional Application No. 61/686,847 filed Apr. 13, 2012, Inventor Ferrand D. E. Corley, the priority of which is claimed.

FIELD OF THE INVENTION

An apparatus to compare and adjust colour reproduction from different light sources.

BACKGROUND OF THE INVENTION

Since man started using fire as a light source, whether this was a wood fire, candlelight, oil lamps or gaslight, these sources of illumination produced relatively smooth distribution of spectral energy across the human visible spectrum (400 to 700 nm). Even when Edison invented the incandescent light bulb, the tungsten element, glowing with heat, produced light having a similarly smooth, full distribution of energy. Consequently, when colored objects were illuminated by any of these light sources the colors looked essentially similar to the average viewer, whose vision compensated for changes in color temperature, i.e. the excessive blue of daylight and lower levels of blue in heat generated illuminants.

With the invention of illuminants having discontinuous spectral distribution such as fluorescent tubes, differences in the appearance of certain colors became very noticeable when viewed under such discontinuous sources. This became particularly relevant with the introduction of color film and television in the 1940s, but was not initially a problem because the prime artificial light sources were full spectrum arc lamps and quartz halogen, the latter a more efficient use of tungsten.

In the 1970's, to reduce air-conditioning loads, studios started using fluorescent and HMI lighting. Since 2010, LED light sources have become increasingly popular in cinema and TV production, because they are lightweight, very efficient and generate even less heat than other types. The downsides are that the light emitted by LED illuminants is discontinuous, there are few if any standards and that LEDs deteriorate with age.

BRIEF SUMMARY OF THE INVENTION

This apparatus seeks to identify differences in the colour reproducing capabilities of different light sources, using internationally accepted TV and Cinema reference color standards, and comprises a front test image which is illuminated by a light source of known spectral characteristics. The front test image contains a plurality of colored and gray toned reference elements. Besides each element there is a 20-75% transparent aperture.

A removable rear test image is located behind the front image having reference elements but no apertures, in a larger but otherwise identical format to the front image. The rear test image is illuminated with light of unknown spectral distribution. One or both of the images is adjustable in x, y and z axes to enable the front and rear images to be aligned.

The reference elements on the rear image can then be viewed through the apertures in the front image by a viewer, camera, or other image reproducing or measuring device which views the elements in perfect alignment. When both front and rear test images are illuminated with light sources having identical spectral distribution at the same brightness levels, then the elements in the front and rear test images will blend and any joins will be imperceptible The various features of novelty which characterize the invention are pointed out with more particularity in the claims annexed to and forming a part of this disclosure. For a better understanding of the invention, its operating advantages and specific objects attained by its use, reference should be made to the accompanying drawings and descriptive matter in which there are illustrated and described preferred embodiments of the invention.

IN THE DRAWINGS

Figure 8:
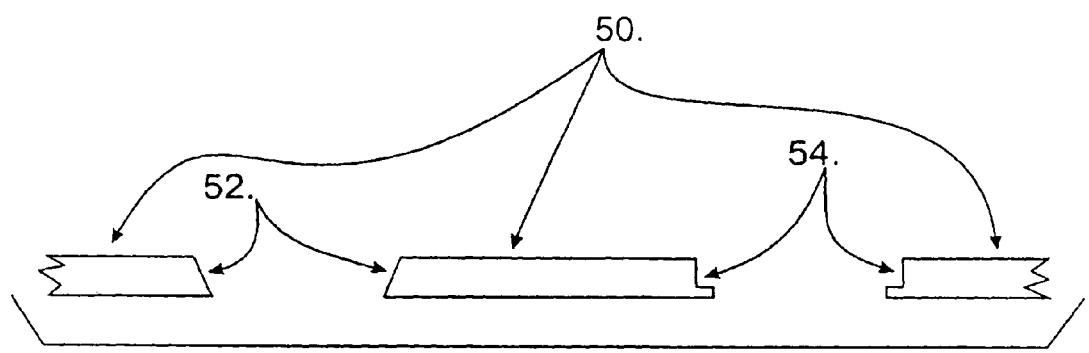
Figure 2:
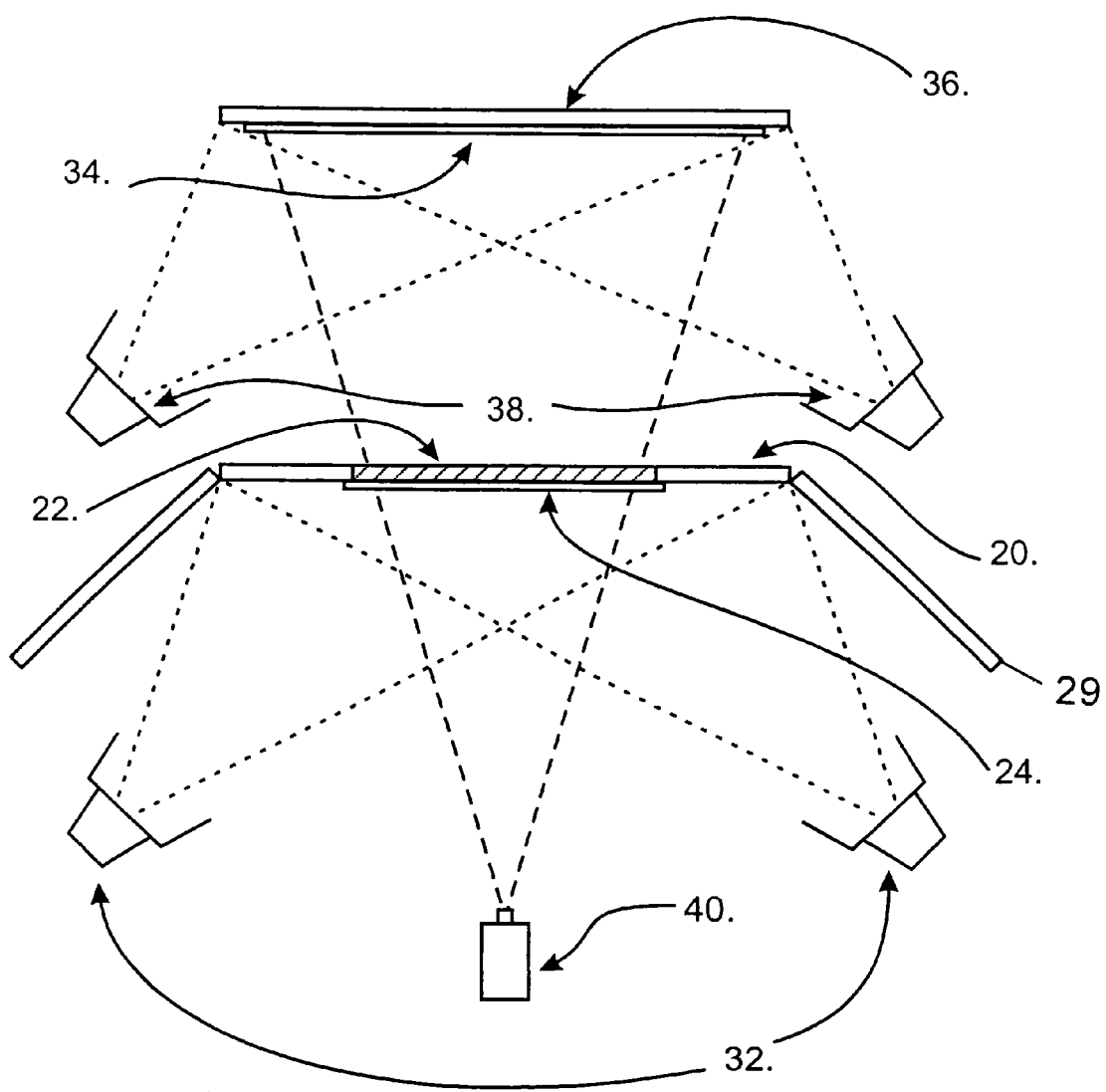
Figure 3:
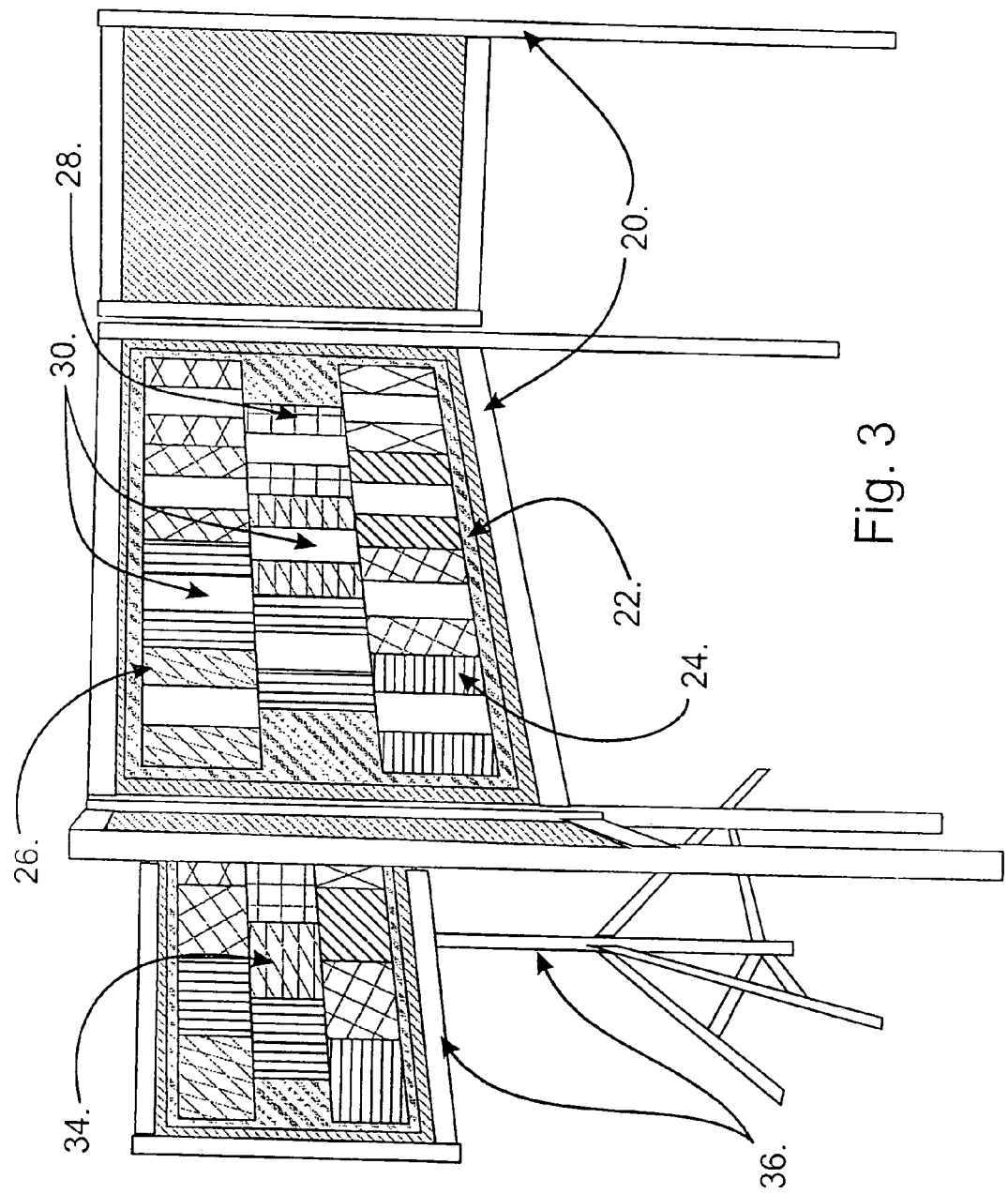
Figure 4:
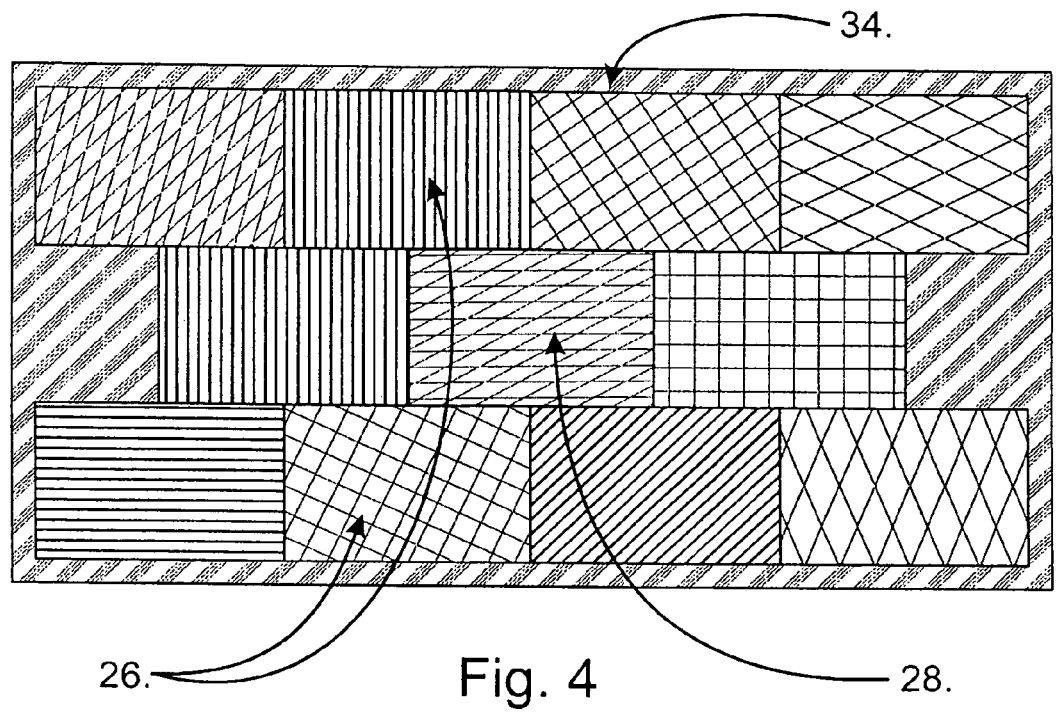
Figure 5:
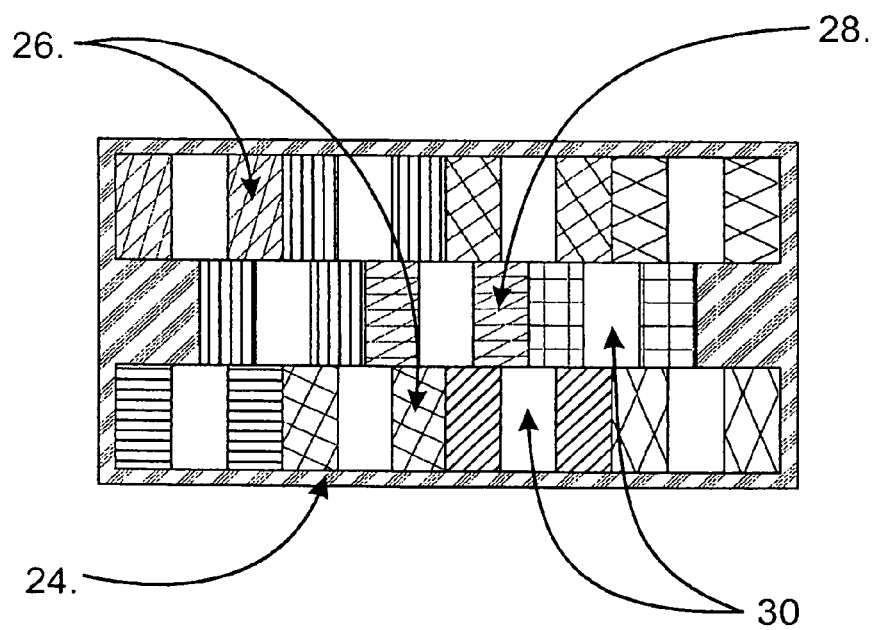
Figure 6:
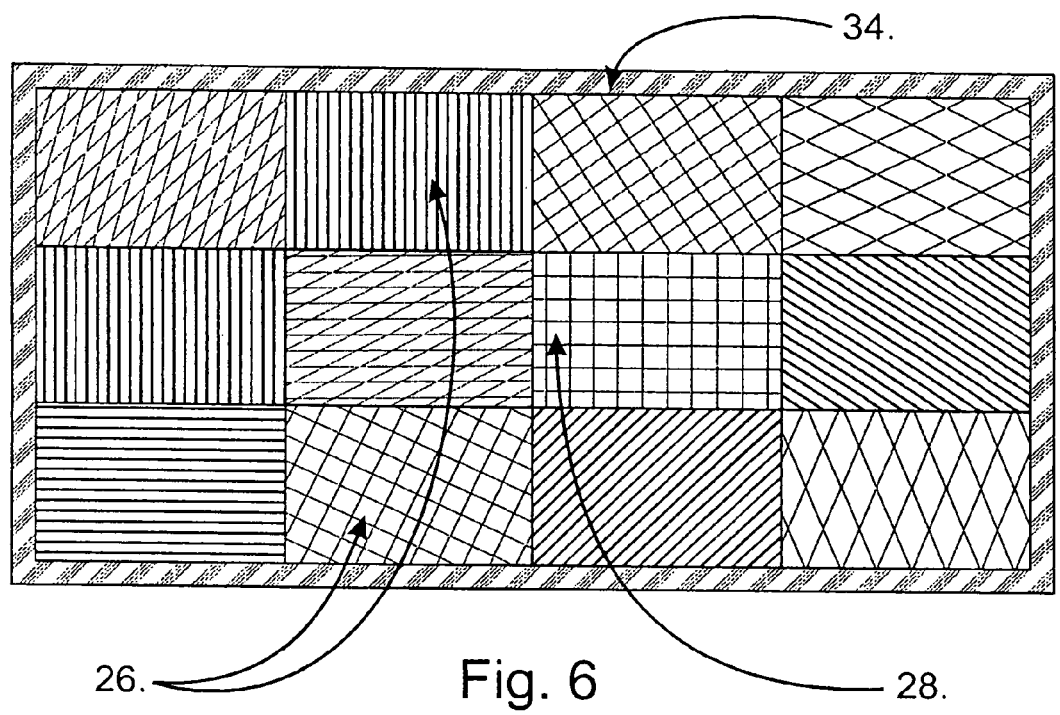
Figure 7:
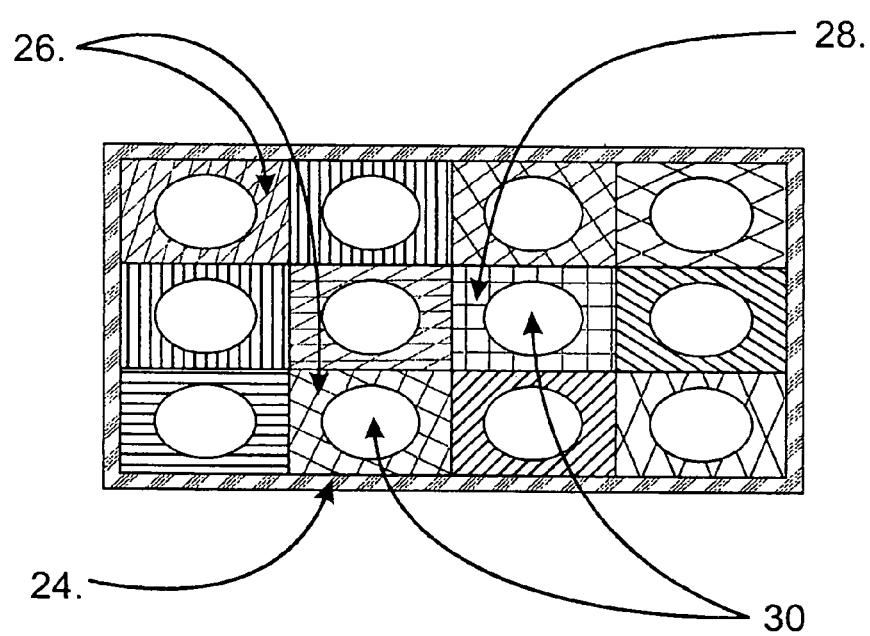

The invention is described by way of illustration with reference to the accompanying drawings in which:

FIG. 1—Illustrates differences in spectral energy distribution between daylight, tungsten and fluorescent light sources compared to the Red, Green and Blue sensitivity curves of the international high definition television standard, ITU-R BT.709;

FIG. 2—is a plan view of one embodiment of the apparatus;

FIG. 3—is a three quarter view of the apparatus;

FIG. 4—is a rear test image comprising a pattern of colored and neutral gray reference elements with alternate rows of references offset;

FIG. 5—shows front test images in the same identical pattern and reference elements as FIG. 4, but reduced in size with each element cut away full height forming apertures to provide a clean electronic scan and greater structural integrity of said front test image;

FIG. 6—shows the same arrangement as FIG. 4, but with the test elements vertically aligned;

FIG. 7—shows the same arrangement as FIG. 6, but with cutaway areas more pleasingly shaped and easier to interpret visually, but less suitable for electronic reproduction but with alternate rows of reference elements aligned and having the cutaway sections of each element surrounded on all sides with the same element; and, FIG. 8—is a plan view of the edges of various apertures.

DESCRIPTION OF A SPECIFIC EMBODIMENT

FIG. 1 illustrates the problem addressed by this apparatus—identifying variations in color reproduction due to the type of light source. The international high definition television standard, ITU-R BT.709 specifies color sensitivity characteristics for the Red (10), Green (12) and Blue (14) camera channels based on illuminant D65 (16). Because the energy distribution in both D65 and tungsten light (18) is smooth and without spikes of energy at any specific wavelengths, it is possible to convert daylight to tungsten and vice versa by applying an appropriate color filter; this enables a camera to reproduce a full spectrum of colors using either light source.

The use of fluorescent (19) and other discontinuous light sources produces excess energy at some wavelengths and too little in other areas of the spectrum. This results in colors reproducing inconsistently, depending on the energy distribution of the light source. This particular fluorescent (19) has a high energy spike centered in the green channel (12) and very low levels of energy in the red (10) and blue (14) channels. The energy spikes in LED and other discontinuous light sources vary both in number and wavelengths across the visible spectrum.

FIGS. 2 and 3, illustrate the invention in one form of apparatus. This comprises front support member (20) with frame (22) holding a front removable test image (24) containing a plurality of colored (26) and gray toned (28) reference elements. Beside each element there is an aperture or transparent area (30). The front removable test image is illuminated with a light source (32) of known spectral distribution.

Side screens (29) are preferably located on either side of the first image to screen light away from the rear image.

A rear removable test image (34) comprising identical colored and gray toned reference elements as in the front test image (24), in the same, but larger format. There are no apertures or cutaway areas, Image (34) is positioned behind the front removable test image on rear support member (36) and is illuminated with lights (38) having different spectral distribution and/or color temperature to the front illuminants (32).

To simplify optical alignment of the two patterns relative to a viewer or reproducing device (40), the rear removable support member (36) is adjustable in X,Y,Z axes and tilt angle using technology well known in the trade.

Once the front and rear images are correctly aligned, it is possible to view the elements of images on the rear image through the apertures in the front image. It will be observed that since the apertures in the front image are beside their respective elements, and the pattern of elements on the rear images the same as the front, without the openings or apertures, it will then be understood that the viewing of the front image and the apertures will permit the viewing of the corresponding elements on the rear image, beside the corresponding elements on the front image, thus enabling the most accurate comparison to be made.

Appropriate adjustments can then be made, to bring the elements on the front and rear images into correspondence with one another.

In order to assist this, the edges of the apertures in the front image may exhibit various formations such as shown in the portions (50) of the front image, and the edges (52, & 54) of the apertures.

Another embodiment (FIG. 6 and FIG. 7) provides for different shaped transparent areas in the colored and gray toned reference elements (26) and (28).

In another embodiment the apparatus may be used to evaluate unknown colors against the known reference of the front image. This is achieved by turning off the rear light source (38) and recording the front test image (24) illuminated by light source (32); this produces a reference colored image having known spectral characteristics with areas of each test element masked. The front lights are then turned off and the rear removable test image (34) is replaced with a solid white or color reference, which is illuminated using rear lights (38) and photographed to produce a mask which when electronically reversed can be used to evaluate unknown colors against the reference colored image having known spectral characteristics using technology that is well known in the trade.

In this further embodiment the corner elements of the front image (24) and rear image (34) have identical reflectance characteristics as the center element, enabling an operator to more easily verify evenness of pattern illumination, using a waveform monitor or other measuring equipment well known in the trade.

Various filters can also be used to produce specific effects for special applications.

The foregoing is a description of a preferred embodiment of the invention which is given here by way of example only. The invention is not to be taken as limited to any of the specific features as described, but comprehends all such variations thereof as come within the scope of the appended claims.

What is claimed is:

1. An apparatus for identifying differences in the visual and recorded appearance of colors and gray tones illuminated by light sources having different spectral distribution and comprising;
   a first panel defining a first side and a second side;
   a first image on said front of said first panel;
   a plurality of separate and different color first elements on said first image;
   a plurality of gray scale first elements on said first image;
   a plurality of apertures in said first panel for respective said separate and different color first elements and said plurality of gray scale first elements;
   a first panel light source for illumination of said first side of said first panel for said first image;
   a second panel spaced rearwardly from said first panel;
   a second image on said second panel behind said first image, said second image defining a plurality of separate and different color second elements and a plurality of gray scale second elements, corresponding to said separate and different color first elements and to said plurality of gray scale first elements of said first image, and said separate and different color second elements and said plurality of gray scale second elements on said second image being viewable through said apertures in said first panel with corresponding separate and different color elements and corresponding gray scale elements adjacent to one another in said first and second images, and,
   a second panel light source located behind said first panel for illumination of said second image.

2. The apparatus as claimed in claim 1 and wherein said apertures in said first panel have angled edges to provide a smooth juncture between first and second images.

3. The apparatus as claimed in claim 1 wherein said apertures in said first panel have edges recessed in said first image whereby to provide a smooth juncture between said first and second images.

4. The apparatus as claimed in claim 1 wherein said apertures are of rectangular shape.

5. The apparatus as claimed in claim 1 wherein said apertures are of non-rectangular shape.

6. The apparatus as claimed in claim 1 wherein said first image illumination is of known spectral characteristics and said second image illumination is unknown spectral characteristics.

7. The apparatus as claimed in claim 1 wherein said first panel defines side edges, and including screen members on either side edge of said first panel obstructing light from said first image illumination and preventing said light from said first image illumination from impinging upon said second image.

* * * * *